(12) United States Patent
Moritzen

(10) Patent No.: US 7,818,259 B2
(45) Date of Patent: Oct. 19, 2010

(54) PREPAID LICENSING SYSTEM AND METHOD

(75) Inventor: Klaus Moritzen, Moehrendor (DE)

(73) Assignee: Siemens Aktiengesellschaft, Munich (DE)

( * ) Notice: Subject to any disclaimer, the term of this patent is extended or adjusted under 35 U.S.C. 154(b) by 1637 days.

(21) Appl. No.: 10/762,517

(22) Filed: Jan. 23, 2004

(65) Prior Publication Data

US 2005/0165693 A1    Jul. 28, 2005

(51) Int. Cl.
*G06F 21/00* (2006.01)
*H04K 1/00* (2006.01)
*H04L 9/00* (2006.01)

(52) U.S. Cl. .......................... 705/59; 705/52
(58) Field of Classification Search .......... 705/59
See application file for complete search history.

(56) References Cited

U.S. PATENT DOCUMENTS

| | | | | |
|---|---|---|---|---|
| 5,671,412 | A * | 9/1997 | Christiano | 707/104.1 |
| 5,758,068 | A * | 5/1998 | Brandt et al. | 726/27 |
| 5,925,127 | A * | 7/1999 | Ahmad | 726/31 |
| 5,933,498 | A * | 8/1999 | Schneck et al. | 705/54 |
| 6,049,789 | A * | 4/2000 | Frison et al. | 705/59 |
| 6,253,193 | B1 * | 6/2001 | Ginter et al. | 705/57 |
| 6,601,046 | B1 * | 7/2003 | Epstein | 705/57 |
| 6,708,157 | B2 * | 3/2004 | Stefik et al. | 705/59 |
| 6,766,305 | B1 * | 7/2004 | Fucarile et al. | 705/51 |
| 6,816,842 | B1 * | 11/2004 | Singh et al. | 705/59 |
| 6,904,528 | B1 * | 6/2005 | Kawanaka | 726/28 |
| 2002/0016775 | A1 * | 2/2002 | Nakagawa | 705/52 |
| 2002/0085720 | A1 * | 7/2002 | Okada et al. | 380/251 |
| 2002/0107809 | A1 * | 8/2002 | Biddle et al. | 705/59 |
| 2003/0028490 | A1 * | 2/2003 | Miura et al. | 705/59 |
| 2003/0135745 | A1 * | 7/2003 | Liu | 713/193 |
| 2004/0117467 | A1 * | 6/2004 | Rich et al. | 709/223 |
| 2004/0128252 | A1 * | 7/2004 | Shirai et al. | 705/59 |
| 2004/0167859 | A1 * | 8/2004 | Mirabella | 705/59 |
| 2004/0205261 | A1 * | 10/2004 | Osada | 710/8 |
| 2005/0038752 | A1 * | 2/2005 | Gaetano et al. | 705/59 |
| 2005/0071280 | A1 * | 3/2005 | Irwin et al. | 705/59 |
| 2005/0138360 | A1 * | 6/2005 | Kamalakantha | 713/156 |

OTHER PUBLICATIONS

"FLEXlm",macrovision, http://www.macrovision.com/products/flexlm/index.shtml.

* cited by examiner

*Primary Examiner*—Andrew J. Fischer
*Assistant Examiner*—C. Aaron McIntyre
(74) *Attorney, Agent, or Firm*—Harness, Dickey & Pierce, P.L.C.

(57) ABSTRACT

A prepaid licensing method permits the prepaid licensing of software on a machine in a secure manner. The method includes storing information for licensing at least one prepaid use of software on a machine. The information, which can be in the form of a software option, includes unique and unchangeable information identifying the machine, and information for measuring a number of uses of the software on the machine. The method includes locally granting a license for the number of prepaid uses of the software on the machine, based upon the stored information.

17 Claims, 4 Drawing Sheets

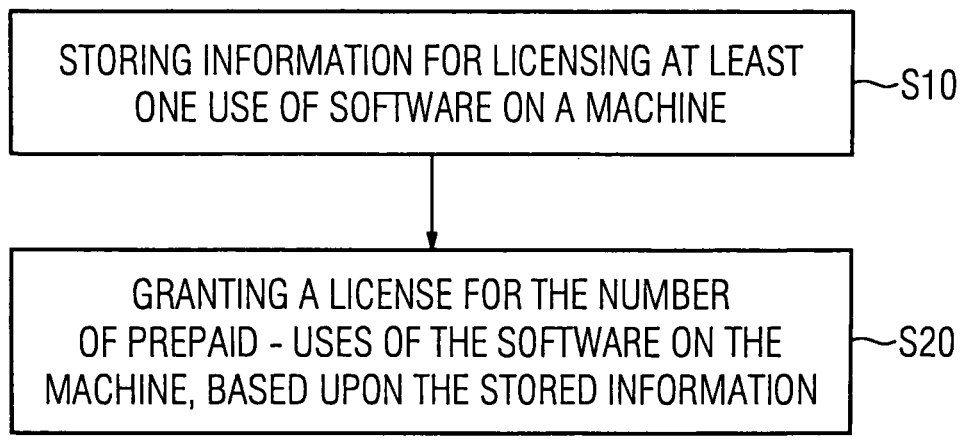
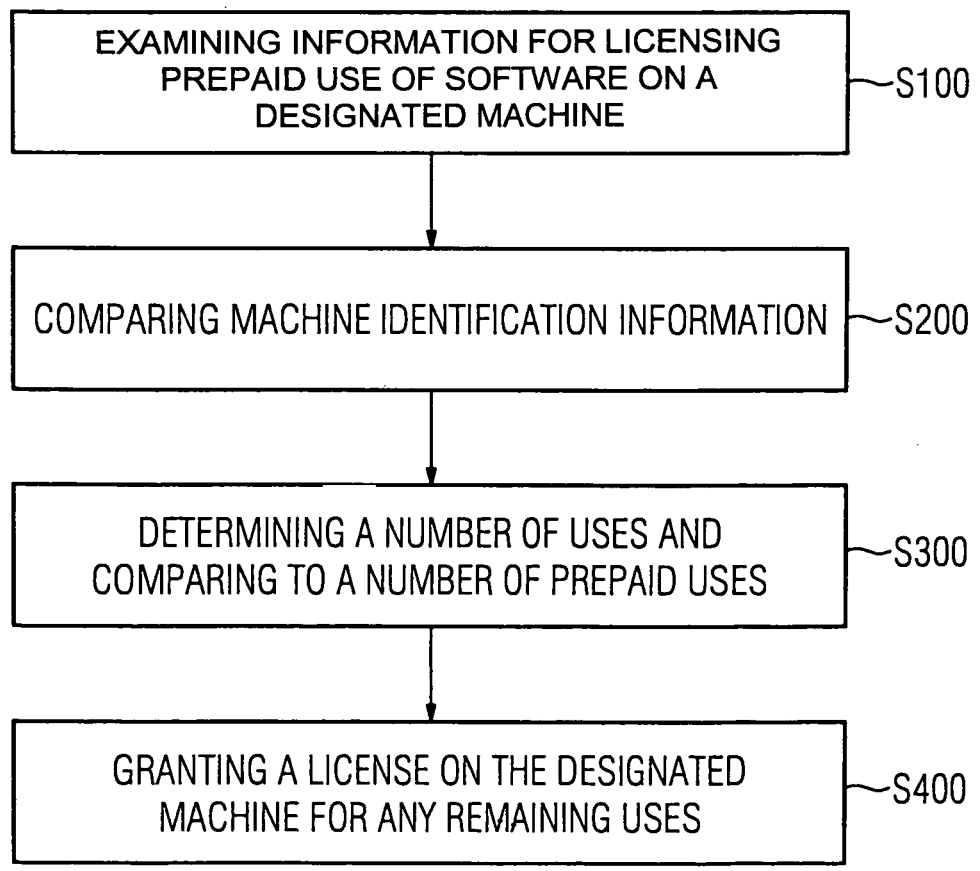

PREPAID LICENSING SYSTEM AND METHOD

FIELD OF THE INVENTION

The present invention is generally related to a licensing system and method.

BACKGROUND OF THE INVENTION

Licensing, in terms of licensing software for example, can be offered in many different ways. These include but are not limited to restricted pay-per-use licenses and licenses without time restriction or without restriction on the number of uses. One problem with unlimited licenses is that many potential clients may avoid taking the license if the licensing fees for such a license, unrestricted by use or time, are too high. If the potential client could pay only for the uses of the license, which can hopefully be passed on to another party, then the potential client may become more interested in licensing the software.

One way of licensing software on a pay-per-use basis is disclosed in U.S. Pat. No. 6,049,789. In such a system, however, each licensee makes contact with the licensor at regular intervals, to pay for each use of the license. Such periodic contact, however, is not always possible.

Flexlm from Macrovision is another software licensing system. In this type of system, calls to the license system are spread over the parts of the code that needs to be licensed. Each call supplies the name of the licensed feature (e.g. FILMING, VIEWER, . . . ) and a version as a parameter. The vendor also supplies a driver to retrieve machine identification safely and to provide this to the licensing system.

The end user then installs a license file on his machine, that he purchased from the vendor. This file contains for each licensed feature information about name, expiration date, and an encrypted license key for example. The system checks the license file and the license is granted. If not, an error is returned. All such systems, however, involve a constant or periodic contact link with the vendor and/or do not involve pre-paid licenses.

With such known licensing systems, contact with the licensor is necessary to pay for a number of uses, monitor uses, attribute particular licenses to particular machines, etc. This can be a problem, especially in the area of licensing software for machines, such as medical devices for example, wherein maintaining a constant or periodic contact link between the licensee and licensor is impossible or at least extremely difficult.

Another way to pay for uses of a product, for example, can be found in the mobile communication field. Here, it is easy for the owner to make periodic contact with the purchaser. Pre-payment can occur by selling a prepaid card, wherein with each use, a contact to the owner is first made. While this is a way to pay for uses of a product, it is not readily applicable to software licenses.

SUMMARY OF THE INVENTION

The present application, in one embodiment, is directed to development of a prepaid licensing method wherein periodic or constant contact with the licensor is not needed. As such, such a method can be applied, for example, to licensing software pertaining, for example, to large machines including but not limited, medical devices (CT scanners, MRI devices, etc.). These large medical devices are often purchased, wherein software and updates are often available and desirable for licensing. Thus, Applicant has recognized a need, and has indeed developed a solution, for a type of pay-per-use method of licensing software, for example.

The method in one embodiment, may include storing a software option for licensing a number of prepaid uses of software for a machine. The software option can include unique and unchangeable information identifying the machine to be licensed, and information for measuring a number of uses of the machine. Based upon the stored information, a license for a number of prepaid uses of the software can be locally granted on the machine. As such, a number of uses of the software can be prepaid without periodic or constant contact and the pay-per-use licensing of the software for the machine can be easily. Further, the software license can be easily tied to a particular machine in a prepaid manner, and thus cheating on the license can be avoided.

Further systems and methods of other embodiments have also been developed. In addition, a program in accordance with an embodiment of the present invention can cause a computer to execute the steps of the aforementioned method.

For fuller understanding of the nature and advantages of the invention, reference should be made to the detailed description of exemplary embodiments taken in conjunction with the accompanying drawings. The detailed description provides only exemplary embodiments of the invention, and thus, the claims of the present invention should not be limited as such.

BRIEF DESCRIPTION OF THE DRAWINGS

The drawings are given by way of illustration only and thus, are not limiting of the present invention, wherein the drawings include:

FIG. 1 illustrates a flow chart of the methodology according to one embodiment of the invention;

FIG. 2 illustrates a flow chart of another embodiment of the invention;

DETAILED DESCRIPTION OF THE PREFERRED EMBODIMENTS

Figure 3:
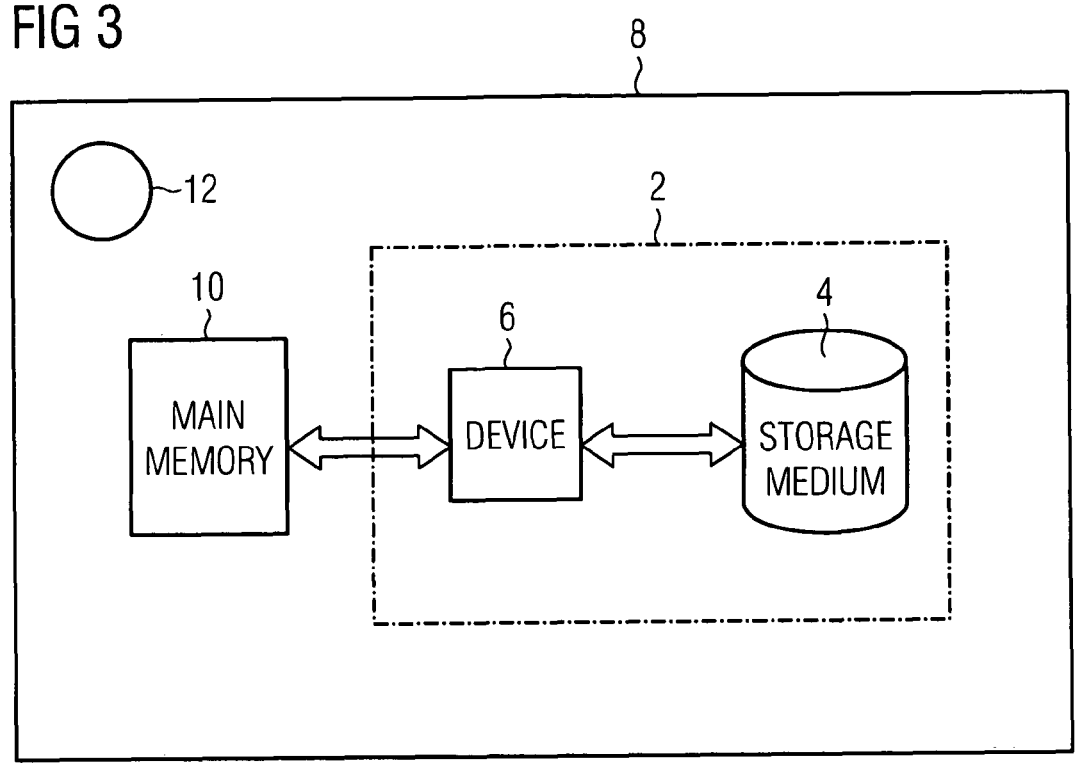
FIG. 3 illustrates a system of an embodiment of the present invention.

In one embodiment, the present application is directed to a prepaid licensing method for licensing, for example, uses of software on a machine, such as software for use in a medical device for example. It should be noted that the machine, throughout the application, may be any device including some type of computer device and preferably including some type of memory, and is not in any way limited to medical devices. The method may include storing information, in the form of a software option, for example, for interacting with the software to be licensed on the machine to permit usage thereof. In should be understood, however, that the software and the software option can also be integrated and stored and used together as one.

The user preferably identifies the software to be licensed, a desired number of uses of the software, the machine identifying information, and potentially a date of when he wants to use the licensed software. The user the pre-pays for these uses of the software. The user is then provided with information, preferably stored in a license.dat file, via a computer readable medium, a computer signal such as an email or Internet download for example, etc.

The stored information is for licensing at least one use of software on a machine. The term software option is used throughout the application to mean some type of software for interacting with existing software to be licensed. The information, such as the software option for example, is preferably stored as a license.dat file, and includes unique and unchangeable information identifying the machine, and information for measuring a number of uses of the software on the machine.

Thereafter, the user can install or copy the information (license.dat file, for example) onto the machine. The method is then able to locally grant a license on the machine for the number of prepaid uses of the software, based upon the stored information. This is done in a transparent manner to the user. As such, constant contact between a licensor and licensee is not necessary. A limited license for the number of prepaid uses of the software can thus be locally granted on the machine without the need for this remote or constant contact.

FIG. 1 of the present application indicates the methodology followed by an embodiment of the present application. In step S10, the method includes storing the information, such as a software option, for licensing at least one use of software on a machine. Thus, via the software option, an arrangement can be made wherein a licensee of the software can license a specific number of uses of the software on the machine. This can be important in software licenses for large medical devices, as one non-limiting example, wherein the medical device (machine) may already have been purchased, but software and its updates for the machine are continuously needed. A pay-per-use system or method of the present application permits the user with the ability to pre-pay for a license of a number of uses of the software, without needing to buy the software or without needing to continuously or periodically contact the licensor. This is done on a prepaid basis by pre-paying for a number of uses of the software via the software option.

The information stored in step S10 includes information identifying the particular machine that will use or license the software. Thus, the licensee of the software must identify a particular machine that will use the software (that will be granted a pay-per-use license for the software), and a unique and unchangeable information identifying the machine that will use the software can then be stored as part of the software option. By doing so, this helps the licensor to limit any potential cheating on the license, such as if the licensee attempted to utilize the software on another machine without having paid for another license.

In addition, by utilizing unique and unchangeable information identifying the machine, constant or periodic contact with the licensor is, again, not necessary. Such unique and unchangeable information identifying the machine can be, for example, some type of machine identification code which uniquely identifies that particular machine. Other examples of such unique and unchangeable information identifying the machine can be a dongle attached to the machine (dongle ID), an Ethernet board address (MAC address) of the machine which is unique in the world, a CPU serial number, or any other mechanism which allows both the licensee and licensor to identify the machine that will be licensed to use the software.

The information stored in step S10 further includes information for measuring a number of uses of the software on the machine. As such, the licensee is able to license a desired number of uses and is able to prepay for such desired number of uses of the software on the machine. By storing information for measuring a number of uses of the software on the machine, the method provides the ability to both pre-pay for a number of uses and monitor the number of uses and to make sure that the number of uses does not exceed the prepaid number.

Finally, in step S20, the method includes granting a license for the number of prepaid uses of the software on the machine, based upon the stored information. Thus, if the information pertaining to a license for a number of prepaid uses of the software is stored on an identified machine, a license can be locally granted for a number of prepaid uses of the software on that identified machine, without the need to continuously contact the licensor. The unique and unchangeable information identifies the machine to use the licensed software, and a number of prepaid uses of the software can adequately be measured.

In the method as shown in FIG. 1, the number of prepaid uses can be monitored or counted. As such, use of the software on the machine can be prohibited upon the count reaching zero. At that time, the licensee can then have the option to go back to the licensor, obtain a new prepaid license agreement for use of the software on the same machine (or for different software and/or a different machine), and can purchase any number of uses of the software in a prepaid fashion.

A determination can be made during start-up, shut-down, or operation of the machine to check on the validity of the software license; namely to determine whether or not the software license is for the correct machine and whether or not at least one prepaid use of the software remains. Accordingly, during start-up, before the machine is actually started and/or before the software is actually run, the methodology set forth in FIG. 1 can take place. Alternatively, this can be monitored during operation of the machine, or can occur as the machine is being shut down.

Further, during the shut-down operation for example, if the last of a number of prepaid uses of the software is being used by the machine, an indication of the expiration or termination of the prepaid license can be conveyed via some type of indication. Such an indication can be audible or visual, for example, via a warning light, warning buzzer, display, etc. Indeed, during any phase of start-up, shut-down, or operation of the machine or of the use of the software, the number of uses of the software remaining on the prepaid license can be determined in any manner, and indicated on the machine in any way.

In addition, in an another embodiment, a threshold can be determined, wherein upon a number of uses remaining actually reaching the threshold, some indication can be conveyed on the machine, either audibly or visually for example. This can act as a type of warning for a user of the machine, indicating that the software license needs to be renewed.

In a further embodiment, it should be noted that at least a portion of the stored information may be encrypted. The encrypted items can include, but are not limited to, the software to be licensed itself, the entire software option, the number of prepaid uses, the unique and unchangeable information identifying the machine to be licensed to use the software, information for measuring the number of uses, etc. The encryption may be used to protect any unauthorized change of any information that could result in the granting of a license that was not paid for. Indeed, all or a portion of any of the stored information may be encrypted.

In addition, the software option itself may be sent via any media and may be sent and/or used in conjunction with any software used on or with the machine. Thus, the software option can be incorporated into any software for use on a machine, such as a medical device for example, and/or can merely be stored and used in conjunction with existing software to ensure that the existing software is licensed in a prepaid and secure manner. Further, the license may additionally be tied to some point of time, such as start-up, operation, or shut-down on the machine, and the stored information pertaining to the license may include some indication of date or time of the last change in the agreement, to even further enhance security and avoid cheating on the license.

The licensing method of the present application is a unique type of prepaid licensing method for a prepaid number of uses of any type of licensable software, which is uniquely tied to a particular machine. As validity of the license can be checked during start-up, operation, or shut-down, cheating of the license agreement can be limited and hopefully even avoided. In one further embodiment of the present application, cheating can further be avoided as follows.

The stored information can include, as part of a file of the licensed software and/or the software option, a "checksum". The checksum can be used for checking various features, such as any changing of the system date. If the system date has been changed, cheating can be recognized, and the number of uses of the software can be reduced, by one for example. Further, the method may include a check to make sure that the licensed software is not taken or copied from one machine, and used on another machine. Further checks can include checking for changes of any values in the stored software and/or software option and/or related file, and checking for any attempts to replace the stored software and/or software option after use of the software, with a file before use. Again, for any found violation, a penalty of, for example, on use, may be enforced.

Regarding any change in values in the stored software and/or software option and/or related file, the license file can include a checksum and can potentially be encrypted. Any change will change the encrypted checksum and thus, can be detected as potential cheat. Regarding the attempt to replace a license file, this can be detected by a next check against the main memory of the system or machine, for example, during use or shut-down for example.

Finally, a check can be made to determine if there is an attempt to replace the stored software and/or software option and/or related file after use, with the stored software and/or software option and/or related file before use. This can be done, for example, while the system or machine is in shut-down and/or when no main memory remains. At this time, this can be detected by use of a time-stamp comparison during start-up, for example.

In one preferred embodiment, at least the software option pertaining to a license is stored for a number of prepaid uses of the software on a machine, and a license check or validation can occur at each start-up of the machine, for example, and/or at each start up of use of the software. An account file or registration entry can optionally be written in for each use and/or can be written in during each shut-down of the machine, for example.

As long as the number of uses remaining for the pre-paid license is greater than zero, the account details of the software license (the license.dat file, for example) are stored in a main memory of the machine, as well as in an account file registration for example, to permit controlling of misuse or cheating. For each use, the following, for example, may be entered into a stored file: date, time of day, identity of the computer device that is used. During each shut-down, the following data, for example, may be entered: date, time of day, identity of computer, event: shut-down. As such, this information can be used to monitor any possible misuse. Finally, if during the start-up of the computer device, the shut-down operation is not discovered as a last entry in the account file, a unit may be removed from the account to reduce the number of uses and to avoid any risk of misuse of the license and/or software.

Again, as previously discussed, this type of methodology for use of a software licensing option of the present application may be used in conjunction with any type of licensable software, including, but not limited to, software for medical devices or machines. By acquiring a license in the manner of the method of an embodiment of the present application, a licensee can acquire, ahead of time, a number of prepaid uses for any type of software.

In another embodiment, following pre-payment, the licensee may be provided with information similar to a type of license key (a license.dat file for example, carried by some type of signal sent via e-mail, over the Internet, or other electronic carrier), wherein in this information can include information pertaining to the software and the licensing of the software based on the pre-paid usage. This information can include the unique and unchangeable information identifying a particular machine on which the software to be licensed is to be run. This unique and unchangeable information can include a dongle ID, an ethernet MAC address, a CPU serial number, etc. The information further includes information relating to the number of uses involved in the prepayment, and can include information identifying a licensing packet or software to be used or licensed and/or, etc. It may further include other information such as an entry date, etc. This licensing key information may thus be in the form of a computer data signal, which may further be encrypted, and which is provided via some medium such as email, the internet, etc., upon receiving payment by the licensor. The key information may then be entered into a machine, for example, for use in conjunction with software to be licensed on the machine, so that the machine, in essence, will now carry units for use of the software during an active term and will store the current number of pre-paid uses of the software in its memory, for example. To protect against manipulations, the information may be encrypted.

As shown in FIG. 2 of the present application, another embodiment of the present application involves a method for granting a prepaid software license on a machine or other configured device. This method can include step S100 of examining information for licensing prepaid use of software on a designated machine. This includes examining information pertaining to a number of prepaid uses of the software on a designated machine. This information can further be a type of software option, and can include unique and unchangeable information identifying the designated machine to use the software being licensed.

In a further embodiment, the step of the examining information may include reading license file contents, such as last usage, date/time; reading license files regarding modification of date/time; reading files of shut-down dates/times, reading start-up dates/times, and/or reading current date/time, etc.

In step S200 as shown in FIG. 2, the method includes comparing machine identification information. This can include comparing information identifying the machine on which the software is to be used, to the unique and unchangeable information identifying the designated machine on which the licensed software is to be run. Subsequent to this step, or even prior to that of step S200, in step S300, a number of uses of the software on the machine is determined and the number of uses is compared to the number of prepaid uses. Finally, in step S400, the license is granted on the designated machine for any remaining uses. This includes granting a license for use of the software, upon the information identifying the machine matching the unique and unchangeable information identifying the designated machine, and upon the number of uses being determined to be less than the number of prepaid uses. Accordingly, as long as the machine using the license corresponds to the designated machine, and as long as at least one prepaid use remains, then the license is granted.

As stated above, in one embodiment the information, in the form of the license.dat file for example, pertaining to the license can include a last usage date/time and a modification date/time. In an effort to further avoid cheating the licensor out of licensing fees, when shut-down, start-up, and/or current date/time are read, a cheat may have occurred if the last shut-down date/time is less than the last usage date/time, the last modification date/time, the start-up date/time, and the current date/time. If so, then by checking these various aspects, a cheat can be detected, and one use (for example) can be removed from the number of prepaid uses of the software license. This can be checked during start-up of the machine to determine attempts to cheat the licensor, for example.

FIG. 3 is an illustration of an embodiment of the present application, including a machine 8, such as a type of medical device for example. The machine 8 can include, there within, a prepaid licensing system. The prepaid licensing system can include a storage medium 4 (which may include the software option, for example), and a device 6. The device 6 is adapted to locally grant a license for the number of prepaid uses of the software on the machine, based upon information stored in the storage medium 4. The storage medium 4 can include at least the software option, and can further include the software to be licensed (wherein the two may also be integrated). It can further include, as part of the software option for example, a unique and unchangeable information identifying the machine to use the licensed software. Finally, it can include information for measuring a number of uses of the software by the machine.

The device 6 may be further adapted to count a number of uses of the software by machine, and be adapted to prohibit operation of the machine upon the count reaching zero. Further, it can be adapted to check on the validity of the software license, in any of the ways previously listed. This can occur, for example, during at least one of start-up, shut-down, and operation of the machine. Specifically, in one embodiment, the device 6 is used to compare the unique and unchangeable information identifying the machine as stored in the storage medium 4, to actual information identifying the machine 8 to be operated. This actual information may be stored in a separate main memory 10 of the machine, or in any other location within the machine. If the comparison does not match, the device 6 will prohibit operation of the machine 8 with respect to the license.

Similar to the embodiments stated before, at least a portion of the information stored in the storage medium may be encrypted. The machine 8 may further be a medical device. The machine 8 itself may include the entire prepaid licensing system 2, or a portion thereof. It preferably stores the software option in any type of memory within the machine, and then uses its own existing computer device to interact with the software option to license the uses of the software. Thus, as shown in FIG. 3, the prepaid licensing system 2 may actual be the machine 8, stored with the software option. The machine 8 may further optionally include some type of indication device 12, such as a visual and/or audible indicator, for indicating that a number of uses is reached and/or that a threshold is reached and/or the number of uses has run out.

Figure 4:
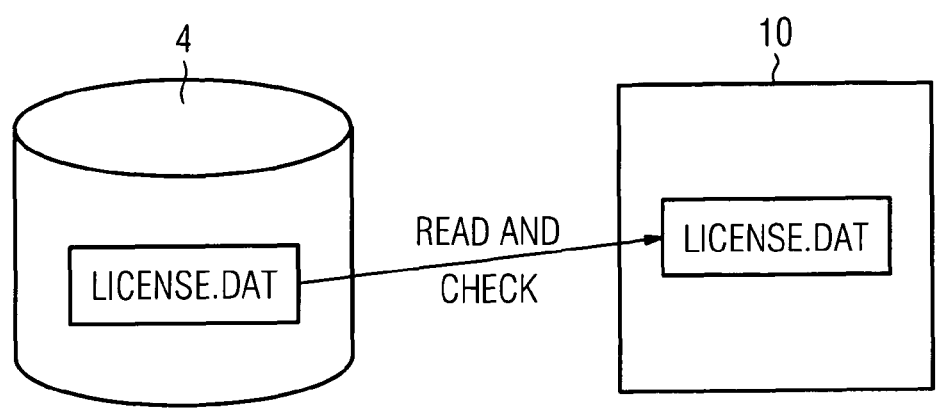
FIG. 4 illustrates one aspect of an embodiment of the present invention during one of software and machine start-up.
Figure 5:
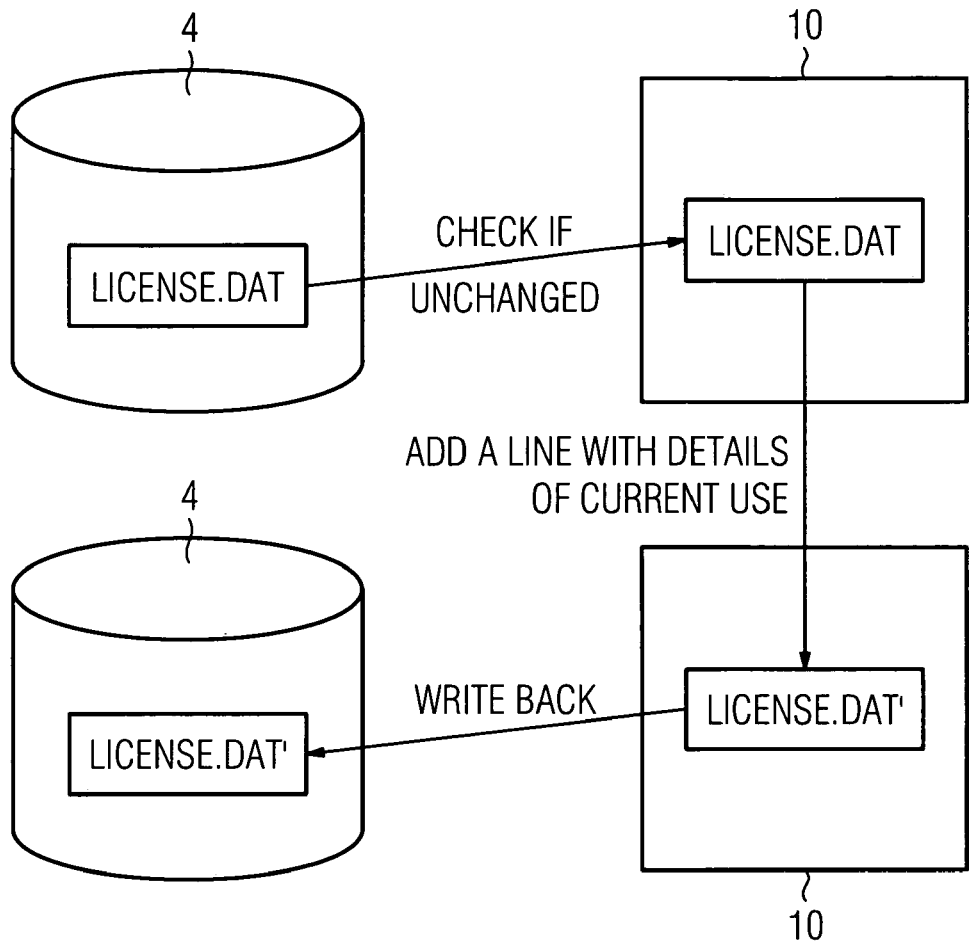
FIG. 5 illustrates one aspect of an embodiment of the present invention during one of software and machine use.
Figure 6:
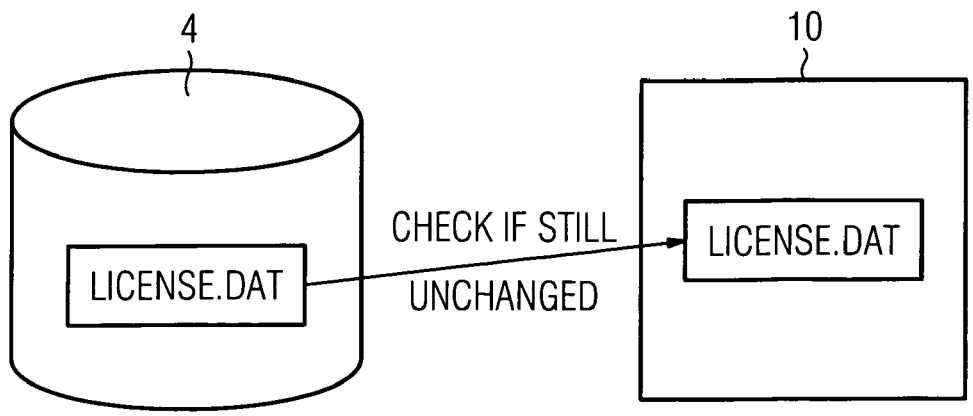
FIG. 6 illustrates one aspect of an embodiment of the present invention during one of software and machine shut-down.

FIGS. 4-6, merely illustrate various aspects of machine or software operation wherein validity of the license may be checked. For example, as shown in FIG. 4, validity of the software license may be checked during start-up, by comparing the information, such as the software option in the form of a license.dat file for example, stored in storage medium 4 to information stored in main memory 10 of the machine 8, including actual information identifying the machine to be operated with the licensed software. The date/time of installation of the license.dat file can be checked, against the date/time of allowable first use of the license (if such information is included in the license.dat file). For example, the date/time of installation of the license.dat file must be at least a one millisecond before the date/time of allowable first use of the license to permit operation thereof. The information, once installed into storage medium 4, is preferably read and stored in main memory 10 of the machine 8 and the start-up steps are checked thereafter (date/time of allowable first use, machine ID, etc.).

Similarly, validity of the software license can be checked in comparison to information stored in main memory 10 of the machine 8, during use of the machine as shown in FIG. 5 and/or during shutdown as shown in FIG. 6. The stored information can be checked and compared (between storage medium 4 and main memory 10) to see if it is unchanged as shown in FIG. 5. Details of the current use can be added and stored, for example. This added information can then be written back from the main memory 10 into the storage medium 4 as shown in FIG. 5, and can be checked to ensure that it is unchanged and/or to count down a usage. Finally, during shut-down, validity of the software license can be checked by comparing information in the storage medium 4 to that of the main memory 10 of the machine 8, usage can be counted down, and information can be stored for comparison at start-up. Note that usage can be counted down during any of start-up, shut-down, and operation.

Figure 7:
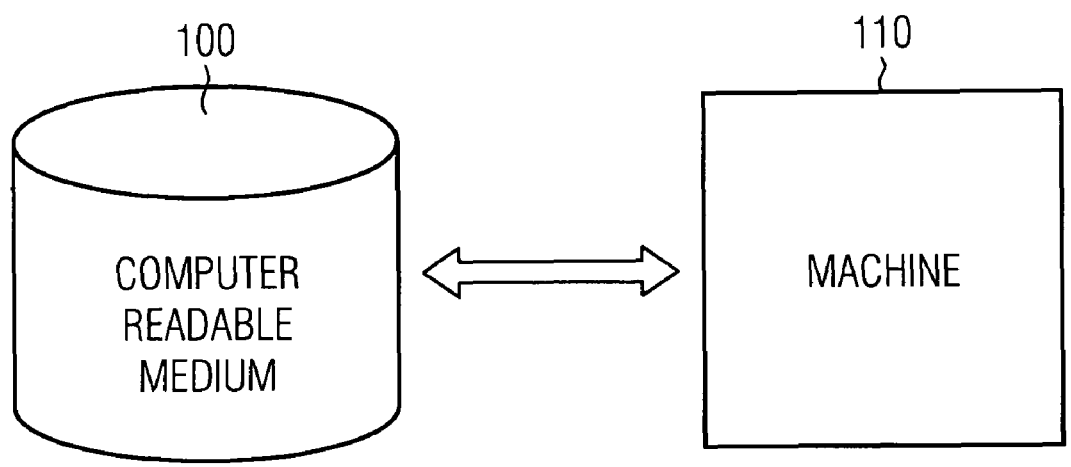
FIG. 7 illustrates interaction between a computer-readable medium and a machine of an embodiment of the present invention.

Finally, the methodology of any of the above-mentioned embodiments of the present application can be embodied in a computer signal as stated above, or on a computer-readable medium 100 as shown in FIG. 7. The computer-readable medium 100 is shown in FIG. 7 as being operable in cooperation with a machine 110, such as a medical device or any other machine adapted to use the software being licensed. The machine 110 is the same as the machine 8 described previously and can include any of the components thereof, such as those shown and described in FIG. 3.

The computer-readable medium 100 can include a first code segment including at least a software option for licensing at least one use of software on a machine. This software option can include unique and unchangeable information identifying the machine and information for measuring a number of uses of the software on the machine 110. Further, the computer-readable medium 100 can include a second code segment, adapted to cause a computer device to locally grant a license for the number of prepaid uses of the software on the machine 110 based upon the information stored in the first code segment. Additional aspects of any of the methodology as discussed above can also be embodied on this computer-readable medium 100.

The computer readable medium 100 may be a built-in medium installed inside a main body of a computer device or machine 110, or a removable medium arranged so that it can be separated from the main body of a computer device or machine 110. Examples of a built-in medium can include, but are not limited to, rewritable involatile memories such as ROMs and Flash memories in hard disks, etc. Examples of the removable medium can include, but are not limited to, optical storage media such as CD-ROMs and DVDs for example; magneto-optical storage media such as MOs for example; magnetism storage media such as floppy disks, cassette tapes, and removable hard disks for example; media with a built-in rewritable involatile memory, such as memory cards for example; and media with a built-in ROM, such as ROM cassettes for example.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for granting a prepaid license on a machine, comprising:
    examining licensing information on a designated machine, the licensing information including information on a prepaid use of software, including a number of prepaid uses of the software and unique and unchangeable information identifying the designated machine;
    comparing information identifying a machine to the unique and unchangeable information identifying the designated machine;
    determining a number of uses of the software on the machine and comparing the number of uses to the number of prepaid uses;
    granting the license for use of the software on the machine for the number of prepaid uses remaining upon the information identifying the machine matching the unique and unchangeable information identifying the designated machine and upon the number of uses being determined to be less than the number of prepaid uses;
    entering into a stored file the date, time of day and identity of the designated machine for each use of the software; and
    examining validity of the software license during each shut-down of the machine by comparing the date, time of day and the identity of the designated machine for each use of the software with the stored file.

2. The method of claim 1, further comprising:
    prohibiting at least one of operation of the software and operation of the machine using the software, with respect to the license, upon the number of uses being determined to be at least equal to the number of prepaid uses.

3. The method of claim 2, further comprising:
    prohibiting at least one of operation of the software and operation of the machine using the software, with respect to the license, upon determining that the comparison does not match.

4. The method of claim 2, wherein at least a portion of the information to be examined is encrypted.

5. The method of claim 2, wherein at least a portion of the information to be examined is stored and encrypted.

6. The method of claim 2, wherein the machine is a medical device.

7. The method of claim 2, further comprising:
    determining a number of uses of the software remaining.

8. The method of claim 2, further comprising:
    determining a number of uses of the software remaining and indicating the number of remaining uses on the machine.

9. The method of claim 2, further comprising:
    determining a number of uses of the software remaining and providing an indication on the machine upon determining that the number of remaining uses exceeds a threshold.

10. The method of claim 8, wherein the indication includes a visual indication.

11. The method of claim 8, wherein the indication includes an audible indication.

12. The method of claim 9, wherein the indication includes a visual indication.

13. The method of claim 9, wherein the indication includes an audible indication.

14. The method of claim 10, wherein the indication includes an audible indication.

15. The method of claim 12, wherein the indication includes an audible indication.

16. The method of claim 1, wherein the information is a software option.

17. The method of claim 16, wherein both the software and the software option are stored.

* * * * *